United States Patent
Hasegawa et al.

(10) Patent No.: US 8,592,491 B2
(45) Date of Patent: Nov. 26, 2013

(54) WATER-BASED RARE EARTH METAL COMPOUND SOL, MANUFACTURING METHOD THEREOF, AND METHOD FOR MANUFACTURING CERAMIC POWDER USING THE SAME

(75) Inventors: Takashi Hasegawa, Omihachiman (JP); Yasunari Nakamura, Yasu-gun (JP); Kazunari Okada, Echi-gun (JP)

(73) Assignee: Murata Manufacturing Co., Ltd., Nagaokakyo-Shi, Kyoto-fu (JP)

(*) Notice: Subject to any disclaimer, the term of this patent is extended or adjusted under 35 U.S.C. 154(b) by 605 days.

(21) Appl. No.: 12/559,738

(22) Filed: Sep. 15, 2009

(65) Prior Publication Data
US 2010/0004116 A1    Jan. 7, 2010

Related U.S. Application Data

(62) Division of application No. 10/569,275, filed as application No. PCT/JP2004/014100 on Sep. 27, 2004, now abandoned.

(30) Foreign Application Priority Data

Oct. 9, 2003 (JP) ................................. 2003-351173

(51) Int. Cl.
*B01F 3/12* (2006.01)
*C01F 17/00* (2006.01)
*C04B 35/468* (2006.01)
*C04B 35/50* (2006.01)
*B01J 23/10* (2006.01)

(52) U.S. Cl.
USPC ........................................... 516/89; 501/139

(58) Field of Classification Search
USPC ........................................... 516/89; 501/139
See application file for complete search history.

(56) References Cited

U.S. PATENT DOCUMENTS

| | | | | |
|---|---|---|---|---|
| 4,537,865 A | * | 8/1985 | Okabe et al. | 501/135 |
| 4,814,128 A | * | 3/1989 | Lieberman et al. | 264/621 |
| 5,225,126 A | * | 7/1993 | Alles et al. | 264/620 |
| 5,297,438 A | * | 3/1994 | Alles et al. | 73/727 |
| 5,417,887 A | * | 5/1995 | Skeele | 516/33 |
| 5,534,468 A | * | 7/1996 | Stephenson | 501/12 |
| 5,624,604 A | | 4/1997 | Yasrebi et al. | |
| 5,944,088 A | | 8/1999 | Feagin | |
| 6,136,048 A | * | 10/2000 | Birchem et al. | 44/354 |
| 6,824,873 B2 | * | 11/2004 | Hattori et al. | 428/403 |
| 7,495,033 B1 | | 2/2009 | Chane-Ching | |
| 2002/0132725 A1 | | 9/2002 | Labarge et al. | |
| 2002/0146365 A1 | * | 10/2002 | Cho et al. | 423/598 |
| 2004/0044088 A1 | | 3/2004 | Chane-Ching | |
| 2004/0192947 A1 | | 9/2004 | Chane-Ching et al. | |
| 2007/0010587 A1 | * | 1/2007 | Hasegawa et al. | 516/89 |

FOREIGN PATENT DOCUMENTS

| | | | |
|---|---|---|---|
| CN | 1162623 | | 10/1997 |
| GB | 2 161 472 A | * | 1/1986 |
| JP | 07-309622 A | * | 11/1995 |
| JP | 11-501609 | | 2/1999 |
| JP | 2003-034526 A | * | 2/2003 |
| JP | 2003-036526 A | * | 2/2003 |
| WO | WO-0138225 A1 | | 5/2001 |
| WO | WO-02/45840 A1 | | 6/2002 |

OTHER PUBLICATIONS

Derwent Abstract on EAST, week 199013, London: Derwent Publications Ltd., AN 1984-310361, JP 59195576 A, (Murata Mfg Co Ltd), abstract.*
Lewis, Richard J., Sr. (2002) Hawley's Condensed Chemical Dictionary (14th Edition), John Wiley & Sons, Online @ http://knovel.com/web/portal/browse/display?_EXT_KNOVEL_DISPLAY_bookid=704&VerticalID=0, headword = Ceramic, (Knovel Release Date: Sep. 4, 2003; downloaded Aug. 21, 2012), pp. 1.*
Girard W. Phelps, John B. Wachtman Jr., Ceramics, General Survey, Ullmann's Encyclopedia of Industrial Chemistry, Ed. Giuseppe Bellussi et al., Published Online: Jun. 15, 2000, DOI: 10.1002/14356007.a06_001, Obtained online @ http://onlinelibrary.wiley.com/doi/10.1002/14356007.a06_001/full.*
Machine Translation of Publ. No. JP H07-309622, published Nov. 1995, Japan patent Office, Tokyo, Japan, obtained online @ http://dossier1.ipdl.inpit.go.jp/AIPN/odse_top_dn.ipdl?N0000=7400 (Downloaded Aug. 22, 2012).*
Machine Translation of Publ. No. JP 2003-036526, published Feb. 2003, Japan patent Office, Tokyo, Japan, obtained online @ http://dossier1.ipdl.inpit.go.jp/AIPN/odse_top_dn.ipdl?N0000=7400 (Downloaded Aug. 22, 2012).*
Machine Translation of Publ. No. JP 2003-036526, published Feb. 2003, Japan patent Office, Tokyo, Japan, obtained online @ http://dossier1.ipdl.inpit.go.jp/AIPN/odse_top_dn.ipdl?N0000=7400 (Downloaded Jul. 1, 2013).*

(Continued)

*Primary Examiner* — Daniel S Metzmaier
(74) *Attorney, Agent, or Firm* — Dickstein Shapiro LLP

(57) ABSTRACT

A particulate subcomponent for a barium titanate dielectric is obtained from a sol in which a rare earth metal compound is dispersed in water. The rare earth metal compound includes a carboxylic acid having at least three carbonyl groups and at least one rare earth metal which can be Sc, Y, La, Ce, Pr, Nd, Sm, Eu, Gd, Tb, Dy, Ho, Er, Tm, Yb, and Lu so that the molar ratio (carbonyl group/rare earth metal) is in the range of 1.2 to 3. A method of making the sol and a method of using the sol to make a ceramic powder is described.

2 Claims, No Drawings

(56) References Cited

OTHER PUBLICATIONS

Machine Translation of Publ. No. JP 2003-034526, published Feb. 2003, Japan patent Office, Tokyo, Japan, obtained online @ http://dossier1.ipdl.inpit.go.jp/AIPN/odse_top_dn.ipdl?N0000=7400 (Downloaded Jul. 1, 2013).*

Vanderbilt Technical Data, DARVAN® 821-A, R.T. Vanderbilt Co., Inc., Norwalk, Conn., USA, obtained online @ http://www.rtvanderbilt.com/TDS_DARVAN_821-A.pdf , (downloaded Jun. 25, 2013), pp. 1-3 (May 2010).*

Vanderbilt Technical Data, DARVAN® Dispersing Agents, R.T. Vanderbilt Co., Inc., Norwalk, Conn., USA, obtained online @ http://web.archive.org/web/20110622013921/http://rtvanderbilt.com/DARVAN_Dispersing_Agents_TDS_Web.pdf , pp. 1-2, (Archive date Jun. 22, 2011—Downloaded Jul. 3, 2013).*

Stojanovic, B.D., et al., Hot-pressed 9.5/65/35 PLZT prepared by the polymeric precursor method, Ceramics International, 2000, vol. 26, No. 6, pp. 625 to 630.

International Search Report dated Mar. 29, 2005, Written Opinion of the International Searching Authority dated Mar. 29, 2005.

Lewis, Richard J., Sr. (2002). Hawley's Condensed Chemical Dictionary (14th Edition). (pp:). John Wiley & Sons. Online version available at http://knovel.com/web/portal/browse/display?_EXT_KNOVEL_DISPLAY_bookid=704&VerticalID=0, two pages.

* cited by examiner

WATER-BASED RARE EARTH METAL COMPOUND SOL, MANUFACTURING METHOD THEREOF, AND METHOD FOR MANUFACTURING CERAMIC POWDER USING THE SAME

This is a division of application Ser. No. 10/569,275, filed Feb. 23, 2006, now abandoned, which is incorporated herein by reference.

TECHNICAL FIELD

The present invention relates to a water-based rare earth metal compound sol, a manufacturing method thereof, and a method for manufacturing a ceramic powder using the same.

BACKGROUND ART

Heretofore, as a dielectric ceramic composition having a high dielectric constant, a $BaTiO_3$-based ceramic has been widely practically used. In order to adjust the temperature properties of the dielectric constant and to improve the sintering properties, addition of various subcomponents has been generally performed. As for multilayer capacitors, the thickness thereof has been decreased year by year in order to increase the static capacity, and in recent years, a product in which the thickness per layer is decreased to several micrometers or less has been commercially available. In this type of capacitor which is composed of thinner layers as described above, the uniformity of materials thereof is increasingly required as compared to that in the past. Hence, subcomponents are required to be made into small particles.

In order to uniformly mix small particle subcomponents with a major component such as $BaTiO_3$, aggregation of fine particles of the subcomponents must be prevented, and hence before being mixed with the major component such as $BaTiO_3$, the subcomponents are preferably present in the form of sol (colloid solution).

Accordingly, in Patent Document 1, a method for manufacturing an organic sol containing a rare earth metal, which is one of the subcomponents, has been proposed.

Patent Document 1: PCT Japanese Translation Patent Publication No. H11-501609

DISCLOSURE OF INVENTION

Problems to be Solved by the Invention

However, since the conventional rare earth metal compound sol disclosed in Patent Document 1 is an organic sol, when the sol is manufactured or is used, an explosion-proof apparatus is required, and as a result, there has been a problem in that the manufacturing cost cannot be easily reduced to a lower level.

The present invention was made in consideration of the current situations described above, and an object of the present invention is to provide a water-based rare earth metal compound sol, which will not cause aggregation of fine particles of a rare earth metal compound, which can be easily handled, and which will not require an explosion-proof apparatus, and is to provide a manufacturing method of the above water-based rare earth metal compound sol. In addition, it is also an object of the present invention to provide a method for manufacturing a ceramic powder, which can manufacture a ceramic powder containing a rare earth metal element uniformly dispersed therein.

Means for Solving the Problems

A water-based rare earth metal compound sol of the present invention is a water-based rare earth metal compound sol containing a rare earth metal compound dispersed in water. In the water-based rare earth metal compound sol described above, the rare earth metal compound contains a carboxylic acid or a carboxylate which has at least three carbonyl groups and at least one rare earth metal selected from the group consisting of Sc, Y, La, Ce, Pr, Nd, Sm, Eu, Gd, Tb, Dy, Ho, Er, Tm, Yb, and Lu, and the molar ratio (carbonyl group/rare earth metal) of the carbonyl group of the carboxylic acid or the carboxylate to the rare earth metal is in the range of 1.2 to 3.

In addition, in the water-based rare earth metal compound sol of the present invention, the carboxylic acid or the carboxylate of the present invention is citric acid or a citrate, respectively.

In addition, a method for manufacturing a water-based rare earth metal compound sol comprises: a step of preparing an acidic or an alkaline aqueous solution of at least one rare earth metal selected from the group consisting of Sc, Y, La, Ce, Pr, Nd, Sm, Eu, Gd, Tb, Dy, Ho, Er, Tm, Yb, and Lu, or a water-based dispersion solution in which a hydroxide of the aforementioned rare earth metal is dispersed; and a step of adding a carboxylic acid or a carboxylate which has at least three carbonyl groups to one of the above solutions so that the molar ratio (carbonyl group/rare earth metal) of the carbonyl group to the rare earth metal is in the range of 1.2 to 3.

In addition, in the method for manufacturing a water-based rare earth metal compound sol, the carboxylic acid or the carboxylate is citric acid or a citrate, respectively.

In addition, a method for manufacturing a ceramic powder comprises: using the water-based rare earth metal compound sol as a subcomponent ingredient.

Advantages

According to the present invention, the water-based rare earth metal compound sol, which will not cause aggregation of fine particles of a rare earth metal compound, which can be easily handled, and which will not require an explosion-proof apparatus, and the manufacturing method of the above water-based rare earth metal compound sol can be provided.

In addition, there can also be provided a method for manufacturing a ceramic powder in which a rare earth metal element is uniformly dispersed therein.

BEST MODE FOR CARRYING OUT THE INVENTION

Next, a method for manufacturing a water-based rare earth metal compound sol, according to the present invention, will be described.

First, a rare earth metal compound in the form of liquid is prepared as an ingredient. The liquid may be either an acidic aqueous solution or an alkaline aqueous solution. In addition, a water-based dispersion solution in which a hydroxide is dispersed in water may also be used. While this aqueous solution or the water-based dispersion solution is being well stirred, a carboxylic acid or a carboxylate, having at least three carbonyl groups, is added so that the molar ratio (carbonyl group/rare earth metal) of the carbonyl group to the rare earth metal is in the range of 1.2 to 3. In order to advance the reaction, heating may be performed. In this step, the rare earth metal ions and the carboxylic acid react with each other to form a polymeric product. When the size of this polymeric product is appropriate, a water-based rare earth metal compound sol (hereinafter simply referred to as "sol") may be formed; however, when the size is excessively large, precipitation occurs, and as a result, the liquid becomes clouded. When the liquid becomes clouded, the pH is adjusted, for example, by operation of adding ammonia water. When the pH of the liquid is increased, the bonds in the polymeric product are appropriately dissociated, and as a result, the size thereof is decreased so that the precipitate is not formed. That is, the liquid is turned into a sol. In order to prevent the precipitation and to form a sol, the average particle diameter must be approximately 150 nm or less. At this stage, the viscosity of the liquid may increase in some cases (gelation), and in this case, dilution is performed using purified water.

When the carboxylic acid or the carboxylate which is to be added has only one or two carbonyl groups, the stability of complexes formed of rare earth metal ions and carboxylic acid becomes insufficient, and as a result, the sol, a polymeric product of the complexes, is also unstable, so that a hydroxide precipitate is formed.

When the carboxylic acid or the carboxylate which is to be added has at least three carbonyl groups, the stability of the complexes is superior, that is, the sol is also stable, and hence a hydroxide precipitate is not formed. Among carboxylic acids or carboxylates, since having a high solubility in water and being capable of manufacturing a sol with a high yield, citric acid or a citrate is preferable.

When the molar ratio (carbonyl group/rare earth metal) of the carbonyl group to a rare earth metal is less than 1.2, precipitation of a hydroxide of the rare earth metal occurs, and when the molar ratio is more than 3, a solution may be formed and a sol may not be formed in some cases.

In order to manufacture a ceramic powder as a raw material for multilayer capacitors or the like by using the sol thus obtained as a subcomponent ingredient, a major component such as $BaTiO_3$ and the sol used as a subcomponent ingredient must be mixed together. For mixing, for example, there may be used a method in which after a slurry composed of a major component such as $BaTiO_3$ and purified water is prepared in a container with a propeller positioned therein, the sol is dripped to the slurry while the slurry is being stirred with the propeller. In addition, a method for manufacturing a ceramic powder, according to the present invention, may also be used for manufacturing a ceramic powder which is used as a raw material for electronic components besides multilayer capacitors.

As an index indicating whether the rare earth metal is uniformly distributed or not in the obtained ceramic powder, a deviation ratio and an intensity ratio are used. Methods for calculating the above indexes will be described.

First, a rare earth metal on the surface of a green compact of a ceramic powder is analyzed by a wavelength disperse X-ray microanalyzer. The measurement area is a square of 81.92 μm by 81.92 μm, this area is divided into 65,536 (256× 256) subareas, and the characteristics X-ray intensity at each subarea is measured.

Even when an analytical element is ideally uniformly distributed in the measurement area, the X-ray intensities at the individual subareas are not equal to each other, and the standard deviation is theoretically the square root of the average X-ray intensity. The actual standard deviation (measured standard deviation) obtained from measurement results cannot be smaller than the theoretical standard deviation and is increased as the degree of segregation of the analytical element is increased. When the deviation ratio is defined as the theoretical standard deviation/the measured standard deviation, and the value thus defined is closer to 1 (is increased), it is understood that the analytical element is more uniformly distributed.

When it is assumed that the analytical element is ideally uniformly distributed in the measurement area, since the intensity distribution becomes the normal distribution, the average value and the median value coincide with each other. However, when the analytical element segregates, the number of measurement subareas having intensities larger than the average value is increased, and as a result, the median value becomes larger than the average value. When the intensity ratio is defined as the median value/average value, and this defined value is closer to 1, it is understood that the analytical element is more uniformly distributed.

Next, the present invention will be described with reference to more detailed examples. In addition, it is to be naturally understood that practical embodiments within the scope of the present invention are not limited only to the following examples.

Example 1

While an aqueous holmium nitrate solution was sufficiently stirred at room temperature, 0.75 moles of triammonium citrate (2.25 moles of carbonyl group) was added relative to 1 mole of holmium. The liquid was clouded. When 3 moles of ammonia water was added to this liquid relative to 1 mole of holmium while the liquid was sufficiently stirred, the liquid became transparent, and a pale red sol was obtained (sample No. 1).

Comparative Example 1

While an aqueous holmium nitrate solution was sufficiently stirred at room temperature, 1.10 moles of sodium tartrate (2.20 moles of carbonyl group), 1.10 moles of oxalic acid (2.20 moles of carbonyl group), or 1.10 moles of sodium citrate (2.20 moles of carbonyl group) was added relative to 1 mole of holmium. The liquid was clouded. Although 3 moles of ammonia water was added to this liquid relative to 1 mole of holmium while the liquid was sufficiently stirred, holmium hydroxide was precipitated (sample Nos. 21 to 23).

Comparative Example 2

While an aqueous holmium nitrate solution was sufficiently stirred at room temperature, 2.20 moles of ammonium acetate (2.20 moles of carbonyl group) or 2.20 moles of lactic acid (2.20 moles of carbonyl group) was added relative to 1 mole of holmium. The liquid was clouded. When 3 moles of ammonia water was added to the liquid relative to 1 mole of holmium while the liquid was sufficiently stirred, a sol was partly formed but was unstable, and as a result, holmium hydroxide was precipitated as the time passed (sample Nos. 24 and 25).

Example 2

When the same operation was performed as that in Example 1 using an aqueous yttrium nitrate solution, a transparent and colorless sol was obtained (sample No. 2).

Example 3

While an aqueous dysprosium nitrate solution was sufficiently stirred at room temperature, 0.75 moles of citric acid was added relative to 1 mole of dysprosium. The liquid was clouded. When 3 moles of ammonia water was added to the liquid relative to 1 mole of dysprosium while the liquid was sufficiently stirred, the liquid became transparent, and a pale yellow sol was obtained (sample No. 3).

Example 4

While an aqueous dysprosium nitrate solution was sufficiently stirred at room temperature, 0.55 moles of ethylenediaminetetraacetate (2.20 moles of carbonyl group) was added relative to 1 mole of dysprosium. The liquid was clouded. When 3 moles of ammonia water was added to the liquid relative to 1 mole of dysprosium while the liquid was sufficiently stirred, the liquid became transparent, and a pale yellow sol was obtained (sample No. 4).

Example 5

A dysprosium hydroxide powder obtained by filtrating and washing a precipitate formed when ammonia water was added to an aqueous dysprosium solution was dispersed in purified water to form a water-based dispersion solution. While this solution was sufficiently stirred at room temperature, 0.75 moles of triammonium citrate was added relative to 1 mole of dysprosium. Since unreacted dysprosium hydroxide partly remained, filtration was performed using a quantitative filter paper No. 5C, so that a pale yellow sol was obtained (sample No. 5).

Example 6

After dysprosium hydroxide was formed by adding ammonia water to an aqueous dysprosium chloride solution, while stirring was sufficiently performed at room temperature, 0.75 moles of triammonium citrate was added relative to 1 mole of dysprosium. While being heated to 60° C., the liquid was continuously stirred so as to advance the reaction. Since unreacted dysprosium hydroxide partly remained, filtration was performed using a quantitative filter paper No. 5C, so that a pale yellow sol was obtained (sample No. 6).

Example 7

When the amount of triammonium citrate to be added relative to 1 mole of holmium was set to 0.40 moles (1.20 moles of carbonyl group), 0.45 moles (1.35 moles of carbonyl group), 0.50 moles (1.50 moles of carbonyl group), 0.80 moles (2.40 moles of carbonyl group), or 1.0 mole (3.00 moles of carbonyl group), and operation equivalent to that in Example 1 was performed, a pale red transparent sol was obtained (sample Nos. 7 to 11). Since sols of sample Nos. 7 and 8 had substantially no fluidity (gelation), dilution with purified water was required; hence, the amount of carbonyl group relative to 1 mole of the rare earth metal was preferably 1.5 moles or more.

Comparative Example 3

When the amount of triammonium citrate to be added relative to 1 mole of holmium was set to 0.20 moles (0.60 moles of carbonyl group) or 1.10 mole (3.30 moles of carbonyl group), and operation equivalent to that in Example 1 was performed (sample Nos. 26 and 27), sample No. 26 formed a precipitate of holmium hydroxide, and sample No. 27 was not a sol but was totally formed into a solution.

The results are collectively shown in Table 1. The average particle diameter was measured by DT-1200 manufactured by Otsuka Electronics Co., Ltd. in accordance with an ultrasonic attenuation method. Distributions of the rare earth metals of ceramic powders formed by mixing $BaTiO_3$ and the liquids of samples Nos. 10, 26, and 27 were measured by a wavelength disperse X-ray microanalyzer, and the deviation ratios, the intensity ratios, and the uniform areas calculated from the measurement results are shown in Table 2.

TABLE 1

| Sample No. | Rare Earth Metal | Carboxylic Acid | Carbonyl Group/Rare Earth Metal (Molar Ratio) | Average Particle Diameter (nm) | Yield (%) | State of Product |
|---|---|---|---|---|---|---|
| 1 | Ho | Triammonium citrate | 2.25 | 10.8 | 85 | Pale Red Transparent Sol |
| 2 | Y | Triammonium citrate | 2.25 | 15.9 | 85 | Colorless Transparent Sol |
| 3 | Dy | Citric acid | 2.25 | No data | No data | Pale Yellow Transparent Sol |
| 4 | Dy | Ethylenediaminetetraacetate | 2.20 | No data | 54 | Pale Yellow Transparent Sol |
| 5 | Dy | Triammonium citrate | 2.25 | No data | 68 | Pale Yellow Transparent Sol |
| 6 | Dy | Triammonium citrate | 2.25 | No data | No data | Pale Yellow Transparent Sol |
| 7 | Ho | Triammonium citrate | 1.20 | 55.8 | No data | High Viscous Pale Red Transparent Sol |
| 8 | Ho | Triammonium citrate | 1.35 | 44.3 | No data | High Viscous Pale Red Transparent Sol |
| 9 | Ho | Triammonium citrate | 1.50 | 42.6 | No data | Pale Red Transparent Sol |
| 10 | Ho | Triammonium citrate | 2.40 | 17.9 | No data | Pale Red Transparent Sol |
| 11 | Ho | Triammonium citrate | 3.00 | 48.0 | No data | Pale Red Transparent Sol |
| 21* | Ho | Sodium tartrate | 2.20 | >300 | — | Precipitate formation |
| 22* | Ho | Oxalic acid | 2.20 | >300 | — | Precipitate formation |
| 23* | Ho | Sodium citrate | 2.20 | >300 | — | Precipitate formation |
| 24* | Ho | Ammonium acetate | 2.20 | >300 | — | Precipitate formation (Partly sol) |
| 25* | Ho | Lactic acid | 2.20 | >300 | — | Precipitate formation (Partly sol) |
| 26* | Ho | Triammonium citrate | 0.60 | 237.2 | — | Precipitate formation |
| 27* | Ho | Triammonium citrate | 3.30 | Measurement not available | — | Solution |

TABLE 2

| Sample No. | State of Liquid | Rare Earth Metal | Deviation Ratio | Intensity Ratio |
|---|---|---|---|---|
| 10 | Sol | Ho | 1.00 | 0.88 |
| 26* | Slurry containing | Ho | 0.87 | 0.82 |

TABLE 2-continued

| Sample No. | State of Liquid | Rare Earth Metal | Deviation Ratio | Intensity Ratio |
|---|---|---|---|---|
| 27* | Precipitate Solution | Ho | 0.91 | 0.77 |

In Tables 1 and 2, sample Nos. provided with * are samples outside the range of the present invention.

As apparent from Table 1, when a carboxylic acid or a carboxylate having only one or two carbonyl groups is used, a hydroxide precipitate is unfavorably formed (see sample Nos. 21 to 25).

Although a carboxylic acid or a carboxylate having at least three carbonyl groups is used, when the molar ratio (carbonyl group/rare earth metal) of the carbonyl group to the rare earth metal is less than 1.2, a hydroxide precipitate is also unfavorably formed (see sample No. 26). On the other hand, when the molar ratio (carbonyl group/rare earth metal) is more than 3, a solution is unfavorably formed (see sample No. 27).

When the yields obtained from the same acidic solution are compared to each other, it is understood that the yield obtained when a citrate is used as the carboxylate (sample Nos. 1 and 2) is higher than that obtained when another carboxylic acid is used (sample No. 4), and hence as the carboxylic acid or the carboxylate, citric acid or a citrate is preferably used.

In addition, as apparent from Table 2, when a ceramic powder is manufactured using a sol as a subcomponent ingredient, as compared to the case in which a slurry containing precipitate or a solution is used, a ceramic powder can be obtained in which the rare earth metal is uniformly distributed.

The invention claimed is:

1. A method for manufacturing a ceramic powder comprising: adding at room temperature a water-based rare earth metal carboxylate sol dispersed in water to a ceramic slurry,
   wherein the sol is formed by combining, with stirring, a carboxylate compound having at least three carboxyl groups with a rare earth metal compound in solution, the carboxylate compound is ammonium citrate, the rare earth metal is at least one member selected from the group consisting of Sc, Y, La, Ce, Pr, Nd, Sm, Eu, Gd, Tb, Dy, Ho, Er, Tm, Yb, and Lu, the molar ratio of carboxyl groups to the rare earth metal is in the range of 1.2 to 2.40, and the ceramic is barium titanate, and
   forming a ceramic powder therefrom.

2. The method for manufacturing a ceramic powder according to claim 1, wherein the rare earth metal solution is an alkaline aqueous solution.

* * * * *